United States Patent [19]
Frankel

[11] Patent Number: 5,894,939
[45] Date of Patent: Apr. 20, 1999

[54] SYSTEM FOR SORTING POST-CONSUMER PLASTIC CONTAINERS FOR RECYCLING

[75] Inventor: Henry Frankel, Edison, N.J.

[73] Assignee: Frankel Industries, Inc., Edison, N.J.

[21] Appl. No.: 08/728,042

[22] Filed: Oct. 9, 1996

[51] Int. Cl.$^6$ .................................................. B07C 7/00
[52] U.S. Cl. .......................... 209/630; 209/588; 209/702; 209/942; 250/223 B; 356/240
[58] Field of Search ........................... 209/576, 577, 209/588, 629, 630, 702, 942; 250/223 B, 223 R; 356/240, 409, 427

[56] References Cited

U.S. PATENT DOCUMENTS

| | | | |
|---|---|---|---|
| 3,358,552 | 12/1967 | Schneider | 88/14 |
| 4,248,389 | 2/1981 | Thompson et al. | 241/101.5 |
| 4,848,590 | 7/1989 | Kelly | 209/564 |
| 4,858,768 | 8/1989 | Plester | 209/3.1 |
| 4,919,534 | 4/1990 | Reed | 356/73 |
| 5,024,335 | 6/1991 | Lundell | 209/618 |
| 5,314,072 | 5/1994 | Frankel et al. | 209/580 X |
| 5,502,559 | 3/1996 | Powell et al. | 250/223 B X |
| 5,699,162 | 12/1997 | Pirani et al. | 209/588 X |

FOREIGN PATENT DOCUMENTS

| | | |
|---|---|---|
| 56-145339 | 11/1981 | Japan . |
| 9116617 | 10/1991 | WIPO ..................... 209/588 |

*Primary Examiner*—Tuan N. Nguyen
*Attorney, Agent, or Firm*—Todd E. Garabedian; Gregory S. Rosenblatt; Wiggin & Dana

[57] ABSTRACT

A method to sort plastic articles, such as bottles, for recycling utilizes a first sensing area where the bottle is irradiated with circularly polarized light. The circularly polarized light changes polarization on passing through the bottle. The changed circularly polarized light is then detected by personnel wearing glasses having filters oriented to block circularly polarized light of a first handedness and produce light characteristic of the composition of the bottle. The bottle is then sorted for recycling by the personnel based upon the composition of the bottle. The method of the invention may be used as described above or in conjunction with a UV light source to identify bottles made from polyethelene napthalene.

12 Claims, 3 Drawing Sheets

SYSTEM FOR SORTING POST-CONSUMER PLASTIC CONTAINERS FOR RECYCLING

CROSS-REFERENCE TO RELATED PATENT

This invention is related to my previous invention described in U.S. Pat. No. 5,314,072 which is herein incorporated by reference in its entirety.

BACKGROUND OF THE INVENTION

1. Field of the Invention

This invention pertains to apparatus and methods for sorting transparent plastic articles such as plastic bottles for recycling, and more particularly to methods of identifying the composition of bottles and sorting the bottles for recycling.

2. Description of the Related Art

The marketability of presorted plastic bottles is significantly greater than the marketability of unsorted plastic bottles. Thus, it is advantageous to sort plastic bottles for recycling into marketable categories. Sortation of plastic beverage and household containers has been performed manually, which is a labor intensive, expensive and often inaccurate process. As recycling efforts in communities increase, so does the need for a faster and more efficient recycling sorting method.

Further, the use of new plastic resins has placed greater demands on the correct identification and sorting of the various types of materials used to produce plastic containers. One such new resin is polyethylene naphthalene (PEN). This resin has superior shelf life and temperature tolerances, but must be identified, sorted, and recycled apart from other plastic resins. Although PEN is similar to other widely used and recycled polyesters such as polyethylene terephthalate (PET) and various grades such as PET-G, PEN must be detected and sorted separately so that processing problems are avoided and the recyclate has satisfactory properties.

Various arrangements have been proposed for sorting recycled materials and are as follows:

- U.S. Pat. No. 4,919,534 to Reed sorts returned glass and PET bottles by testing the material with polarized and colored light. Alternately flashing red and green polarized light is optically detected as the light passes through the bottle. The rotation of the polarized light differentiates between glass and PET.
- U.S. Pat. No. 4,858,768 to Plester removes plastic bottles which have been contaminated prior to their arrival at the sorting center. Warm water is injected into the plastic bottle, agitated, and various residue analyzers determine the characteristics of the residue. For example, electromagnetic radiation, light scattering, polarized light rotation, and X-ray fluorescence may be used to examine the residue.
- U.S. Pat. No. 4,248,389 to Thompson et al. discloses a detector which sorts recycled bottles by scanning the Universal Product Code (UPC), using that code to classify the bottle, and sorting the bottle into the appropriate bin for later reclamation.
- U.S. Pat. No. 3,358,552 to Schneider discloses sorting bottles by optically determining the placement of a label, the color of the bottle, and the pattern engraved in the glass. The outlets of these sensors are fed into a logic circuit, which then determines the commercial affiliation of the bottle by determining the combination of the triggered detectors.
- U.S. Pat. No. 4,848,590 to Kelly discloses sorting different types of scrap metal on the basis of their X-ray fluorescence. Depending on the type of metal detected, the metal is directed to various storage areas.
- Japanese Patent No. 56145339 generally discloses detecting chlorine in a vinyl chloride resin to determine the degree of aging of the resin.
- U.S. Pat. No. 5,024,335 to Lundell discloses a mechanical sorter for removing large plastic containers and aluminum cans from other refuse. A variety of refuse is transported below rotating brushes. Those containers which are too large to fit under the brushes are lifted off the conveyors and over the top of the brushes. After the containers pass over the top of the brushes, they are diverted to a separate conveyor for later removal.

Despite all the effort toward the development of recycling methods and apparatus, further improvement is needed. Furthermore, existing detection and sorting equipment are required to detect new types of packaging resins. This invention meets these needs.

SUMMARY OF THE INVENTION

In one aspect, the present invention is directed to a method of sorting transparent plastic articles such as bottles for recycling. By transparent, it is meant that light of a desired wavelength will pass through the article.

One method of the invention comprises the steps of conveying a bottle via a conveying means to a first sensing area comprising a light source and a first plurality of filters. The first plurality of filters filter the light from the light source and transmit circularly polarized light of a first handedness. The bottle to be identified and recycled is irradiated with the circularly polarized light, whereby the circularly polarized light changes polarization upon passing through the bottle. The changed circularly polarized light is then detected by personnel wearing glasses comprising a second plurality of filters. The second plurality of filters are oriented to block circularly polarized light of the firsthandedness and produce light characteristic of the composition of the bottle. The bottle is then sorted for recycling by the personnel based upon the composition of the bottle. Thus, bottles made from polyvinyl chloride (PVC), polyethylene terephthalate (PET), and PET-G may be easily identified and sorted at minimal cost.

The method of the invention may be used as described above or in conjunction with an additional identifying step comprising conveying the bottle to a second sensing area with a UV light source, and irradiating the bottle with UV light. Bottles made from polyethylene naphthalene (PEN) are easily identified and sorted by the characteristic glow of the bottle upon exposure to UV light.

BRIEF DESCRIPTION OF THE DRAWINGS

The invention will be more fully understood from the following detailed description taken in conjunction with the accompanying drawings in which.

DETAILED DESCRIPTION

Figure 1:
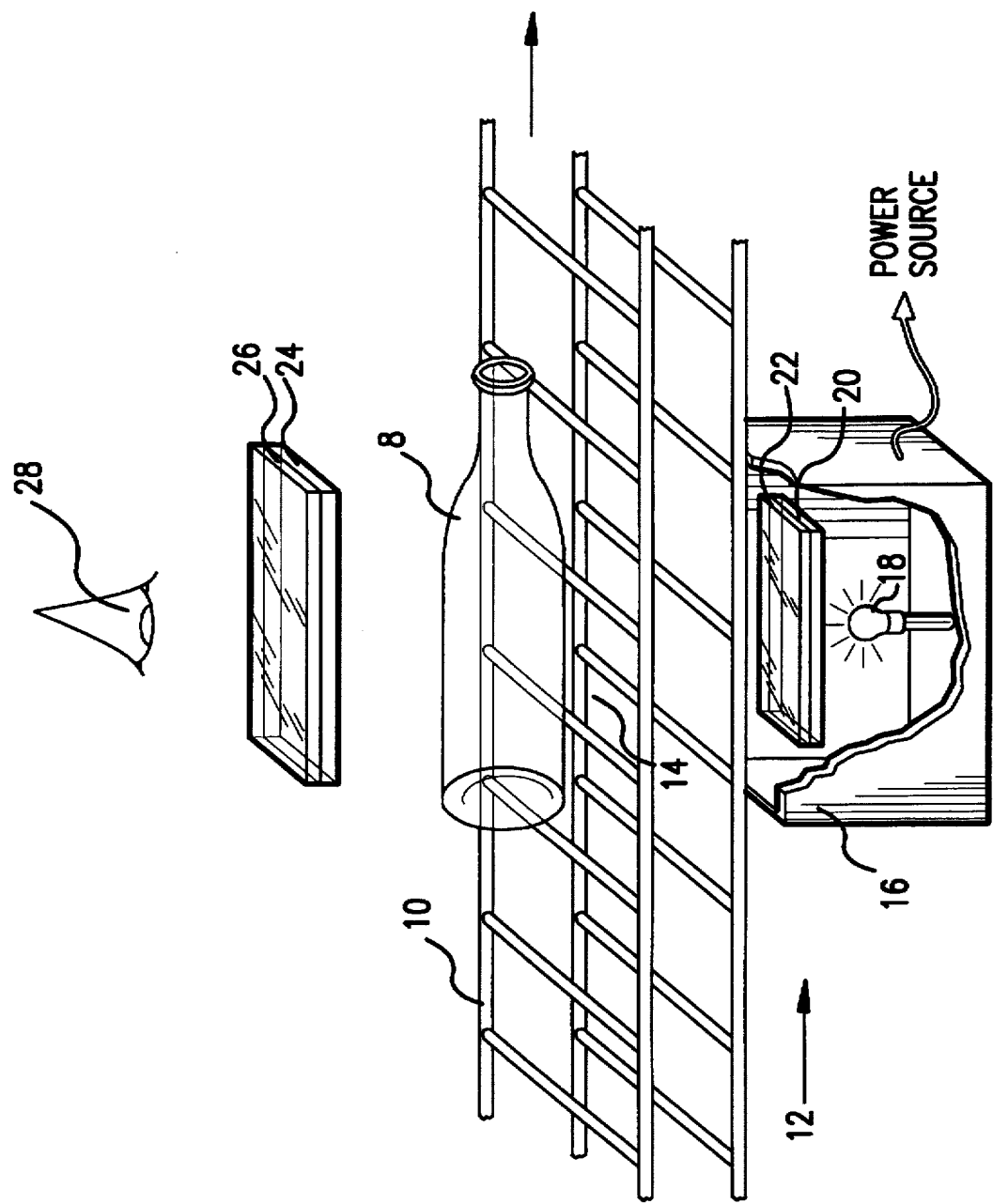
FIG. 1 is a diagram of one embodiment of the invention.

As shown in FIG. 1, a bottle 8 to be sorted and recycled is placed on a main conveyor 10 which moves the bottles in a longitudinal direction 12. The conveyor 10 is preferably made from a wire mesh or net that allows light to pass through unimpeded. The bottle starts at the beginning or "upstream" end of the system, and travels to a terminal or "downstream" end.

A sensing area 14 is produced by light coming from a light box 16 mounted below the conveyor 10. The light box 16 consists of a light source 18 of fluorescent or incandescent bulbs connected to a power source, and a plurality of filters that produce circularly polarized light from the light emitted from the light source 18. The circularly polarized light is directed through the bottle 8 lying on the conveyor 10.

The plurality of filters preferably comprise a linear polarizing filter 20 disposed above the light source 18 and a quarterwave plate 22 disposed over the polarizing filter 20. The quarterwave plate 22 is preferably made of a birefringent material whose thickness delays either the vertical or the horizontal component of the light by one quarterwave length with respect to the other. The quarterwave plate 22 is rotationally oriented with respect to the linear polarizing filter 20 so that the phase lead and phase lag directions of the quarterwave plate 22 are 45 degrees from the polarization direction of linear polarizer 20. Thus, circular polarized light is transmitted from the combination of filters and passes through the bottle 8. Circularly polarized light of either right- or left-handedness may be produced using selected filters.

Sorting personnel are situated on the other side of the conveyor 10 to identify and sort the bottles. The sorting personnel are equipped with glasses that receive the light emitted from the bottle 8. The glasses worn by each of the sorting personnel include a plurality of filters including a quarterwave plate 24 and a linear polarizing filter 26. The quarterwave plate 24 is attached to the linear polarizing filter 26 such that the linear polarizing filter 26 is between the quarterwave plate 24 and the eyes of the sorter 28. Thus, the eyes of the sorting personnel 28 serve as the detector. The linear polarizing filter 26 and the quarterwave plate 24 located on the glasses of the sorting personnel are oriented to filter out the left or right handed circularly polarized light produced by the linear polarizing filter 20 and quarterwave plate 22. Thus, if the quarterwave plate slow direction is 45 degrees clockwise from the polarization direction of the filter, then the quarterwave plate should be oriented 45 degrees clockwise with respect to the polarizing direction of the filter. Once the quarterwave plate is in a fixed position with respect to the linear filter, the physical orientation of the circularly polarized filters at the emitter and detector does not matter. It is to be understood that right handed circular polarizer may be used as a filter for the emitter rather than the detector so long as the detector has the opposite (i.e., left handed) circular polarization.

It is preferable to pass the light leaving the emitter 18 through a linear polarizing filter 20 and then through a quarterwave plate 22 to produce circularly polarized light of first handedness. When determining the change in polarization of the light, it is preferable to pass the light leaving the bottle through a second quarterwave plate 24 followed by a second linear polarizing filter 26. In addition, the relative orientation of the quarterwave plate 24 with respect to the linear polarizing filter 26 on the glasses of the sorting personnel are such to only block light that is circularly polarized in the first handedness.

The light leaving the light source 18 which passes through the linear polarizing filter 20, quarterwave plate 22, bottle 8, glasses-mounted quarterwave plate 24, and glasses-mounted linear polarizing filter 26, respectively, is received at the eye of the sorter 28. Thus, the sorting personnel determine whether the light has changed polarization by passage through the bottle. Such a change in polarization by containers made of different types of plastic resin is characterized by the appearance of the bottle through the glasses of the personnel sorting the containers. The appearance of the bottles is characterized by changes in the intensity and uniformity of the lighting of the bottles. For example, PET bottles appear bright and uniform as if lit from within by a light bulb. PVC bottles, on the other hand, appear dark. Bottles made from PET-G are characterized by changes in color such as the appearance of a rainbow effect on parts of the bottle. The appearance is a function predominantly of the type of resin and modified by its mode of manufacture during blow molding and is used to sort the containers by type. Thus, the appearance of the bottle seen through the glasses serves as the visual clue as to the type of plastic and is deposited in the appropriate storage container.

Figure 2:
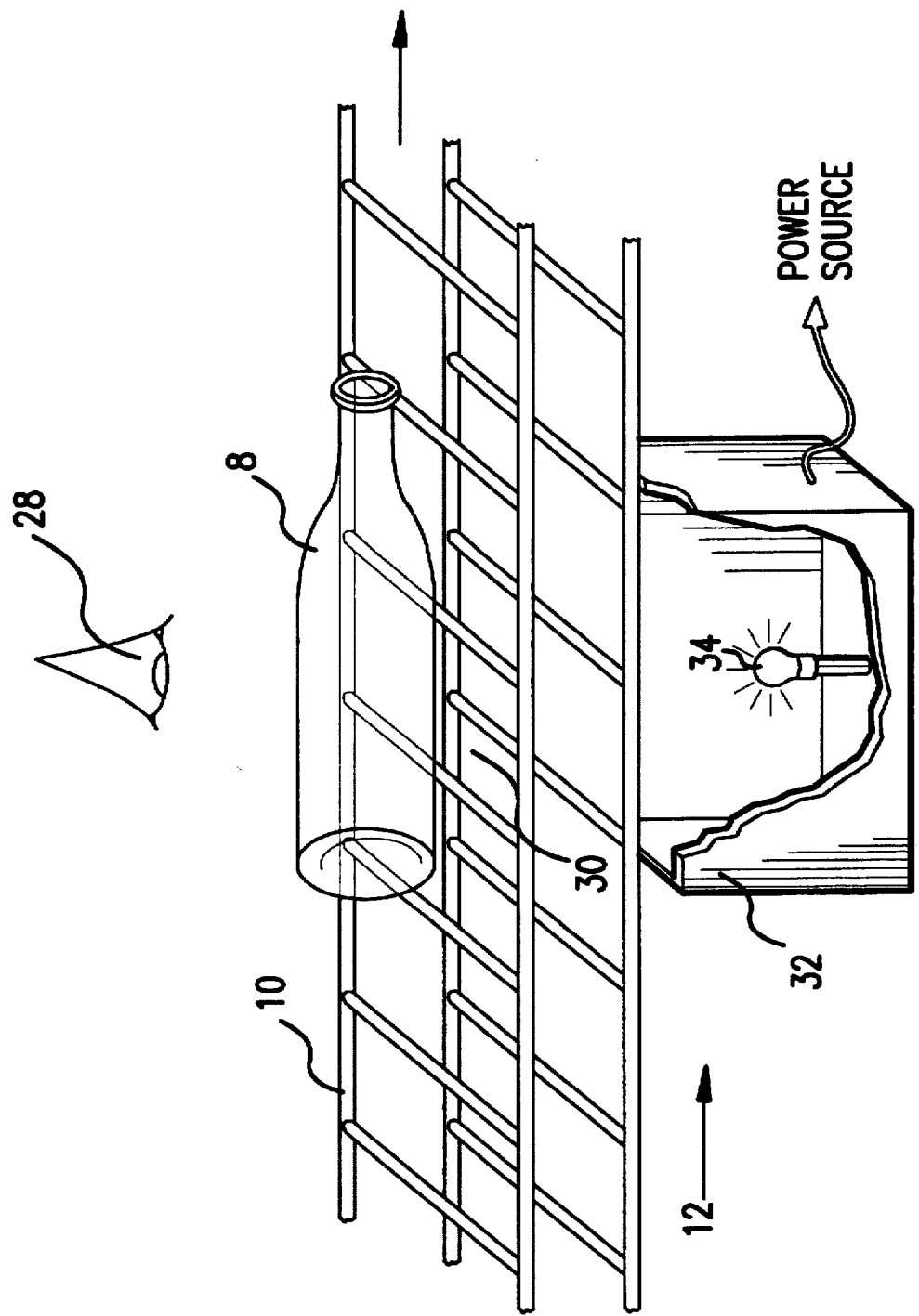
FIG. 2 is a diagram of another embodiment of the invention.

During and/or after passing through the circularly polarized sensing area 16, the bottle may be further identified by exposure to UV radiation. As shown in FIG. 2, the bottle 8 is conveyed on the conveyor 10 to a second sensing area that includes a UV emitting bulb 34 in a light box 32. Containers irradiated with UV radiation and composed of polyethylene naphthalate (PEN) radiate a glow due to the fluorescence of the PEN molecule. The emitted fluorescence is detected by the eyes of the sorting personnel without the aid of filters, and bottles made from PEN may be easily identified and sorted for proper recycling.

Figure 3:
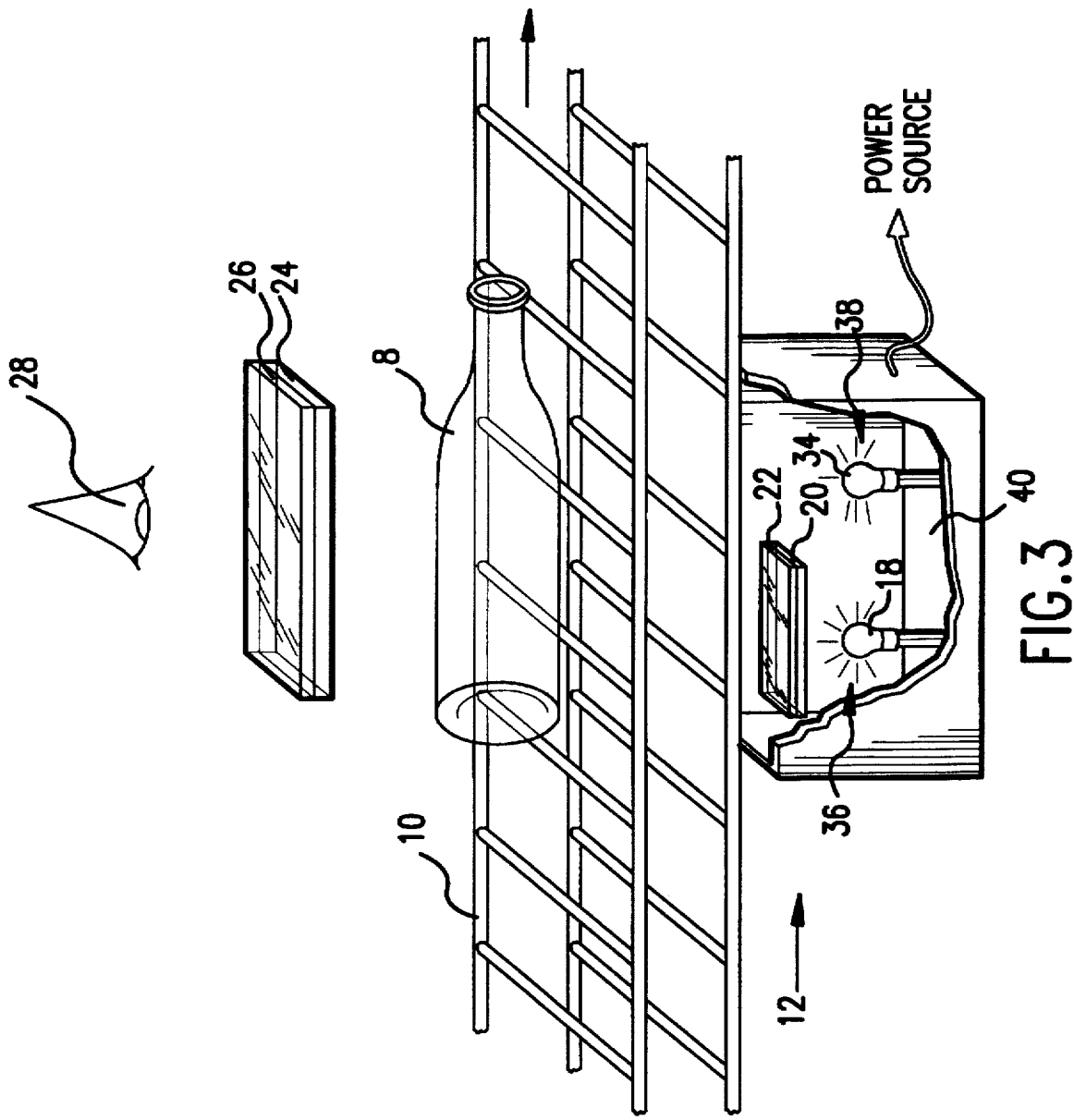
FIG. 3 is a diagram of yet another embodiment of the invention.

FIG. 3 illustrates another embodiment of the invention in which a circularly polarized light source 36 and a UV light source 38 are combined in a single light box 40. As described above, the circularly polarized light source consists of a light source 18 of fluorescent or incandescent bulbs connected to a power source, and a plurality of filters that produce circularly polarized light from the light emitted from the light source 18. The circularly polarized light is directed through the bottle 8 lying on the conveyor 10. As described above, the plurality of filters preferably comprises a linear polarizing filter 20 disposed above the light source 18 and a quarterwave plate 22 disposed over the polarizing filter 20. The light box 40 also includes a UV emitting bulb 34 to identify PEN-based bottles as described above. Sorting personnel are equipped with glasses that receive the circularly polarized light to identify PET, PVC, and PET-G based bottles. Thus, the eyes of the sorting personnel 28 serve as the detector.

Although the invention has been described with respect to recycling of plastic bottles, it is to be understood that any recyclable, transparent, plastic article may be identified and sorted using the method of the invention.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents, patent application and other publications cited herein are incorporated by reference in their entirety.

What is claimed is:

1. A method of sorting plastic articles for recycling, comprising the steps of:

conveying a plastic article via a conveyor to a first sensing area comprising a light source and a first plurality of filters, said first plurality of filters filtering the light from said light source to produce circularly polarized light of a first handedness;

irradiating said plastic article with said circularly polarized light, said circularly polarized light changing polarization upon passing through said plastic article;

detecting said changed circularly polarized light by personnel wearing glasses, said glasses comprising a second plurality of filters, said second plurality of filters oriented to block circularly polarized light of said first handedness and transmit said light characteristic of the composition of said plastic article; and sorting said plastic article for recycling by said personnel based upon the composition of said plastic article.

2. The method of claim 1, wherein said first plurality of filters comprises a linear polarizing filter and a quarter wave plate.

3. The method of claim 1, wherein said second plurality of filters comprises a linear polarizing filter and a quarter wave plate.

4. The method of claim 1, wherein the composition of said plastic article is selected from the group consisting of PVC, PET, and PET-G.

5. The method of claim 4, wherein said plastic article is a bottle.

6. A method of sorting plastic articles for recycling, comprising the steps of:

conveying a plastic article via a conveyor to a first sensing area comprising a light source and a first plurality of filters, said first plurality of filters filtering the light from said light source to produce circularly polarized light of a first handedness;

irradiating said plastic article with said circularly polarized light, said circularly polarized light changing polarization upon passing through said plastic article;

detecting said changed circularly polarized light by personnel wearing glasses, said glasses comprising a second plurality of filters, said second plurality of filters oriented to block circularly polarized light of said first handedness and transmit light characteristic of the composition of said plastic article;

conveying said plastic article via said conveyeor to a second sensing area, said second sensing area comprising a UV light source;

irradiating said plastic article with UV light;

determining the composition of said plastic article by light emitted by said irradiated plastic article; and sorting said plastic article for recycling by said personnel based upon the composition of said plastic article.

7. The method of claim 6, wherein the composition of said plastic article is PEN.

8. The method of claim 6, wherein said plastic article is a bottle.

9. A method of sorting bottles for recycling, comprising the steps of:

conveying a bottle via a conveying means to a sensing area comprising
a first light source and a first plurality of filters, said first plurality of filters filtering the light from said light source to produce circularly polarized light of a first handedness; and
a second light source producing UV irradiation;

irradiating said bottle with said first light source and said second light source, said circularly polarized light changing polarization upon passing through said bottle;

detecting said changed circularly polarized light by personnel wearing glasses, said glasses comprising a second plurality of filters, said second plurality of filters oriented to block circularly polarized light of said first handedness and produce light characteristic of the composition of said bottle;

determining the composition of said bottle by light emitted by said UV-irradiated bottle; and sorting said bottle for recycling by said personnel based upon the composition of said bottle.

10. The method of claim 9, wherein said first plurality of filters comprises a linear polarizing filter and a quarter wave plate.

11. The method of claim 9, wherein said second plurality of filters comprises a linear polarizing filter and a quarter wave plate.

12. The method of claim 9, wherein the composition of said bottle is selected from the group consisting of PVC, PET, PEN, and PET-G.

* * * * *